United States Patent
Cronin et al.

(10) Patent No.: US 11,361,864 B2
(45) Date of Patent: Jun. 14, 2022

(54) TRACKING USAGE OF A PULSE OXIMETER VIA A NETWORK SYSTEM

(71) Applicant: KONINKLIJKE PHILIPS N.V., Eindhoven (NL)

(72) Inventors: John Cronin, Bonita Springs, FL (US); Steven Philbin, Bonita Springs, FL (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1057 days.

(21) Appl. No.: 15/777,341

(22) PCT Filed: Nov. 10, 2016

(86) PCT No.: PCT/EP2016/077232
§ 371 (c)(1),
(2) Date: May 18, 2018

(87) PCT Pub. No.: WO2017/089139
PCT Pub. Date: Jun. 1, 2017

(65) Prior Publication Data
US 2021/0202084 A1    Jul. 1, 2021

Related U.S. Application Data (60) Provisional application No. 62/259,064, filed on Nov. 24, 2015.

(30) Foreign Application Priority Data

Mar. 17, 2016  (EP) .................................. 16160943

(51) Int. Cl.
*G16H 40/67* (2018.01)
*G16H 10/60* (2018.01)

(52) U.S. Cl.
CPC ............. *G16H 40/67* (2018.01); *G16H 10/60* (2018.01)

(58) Field of Classification Search
CPC ........ G16H 40/67; G16H 15/00; G16H 40/63; A61B 5/14551; A61B 5/02416; A61B 5/1455
See application file for complete search history.

(56) References Cited

U.S. PATENT DOCUMENTS

| 8,639,307 | B2 | 1/2014 | Fein | |
| 2004/0102683 | A1* | 5/2004 | Khanuja | H04L 67/2838 600/300 |

(Continued)

FOREIGN PATENT DOCUMENTS

| CN | 102811242 A | 12/2012 |
| JP | 2012196330 | 10/2012 |

(Continued)

OTHER PUBLICATIONS

T. Polk, W. Walker, A. Hande and D. Bhatia, "Wireless telemetry for oxygen saturation measurements," 2006 IEEE Biomedical Circuits and Systems Conference, 2006, pp. 174-177, doi: 10.1109/BIOCAS.2006.4600336 (Year: 2006).*

*Primary Examiner* — Joseph D Burgess (57) ABSTRACT

A method for tracking usage of a pulse oximeter via a network system comprising: uploading a patient information with corresponding pulse oximeter identification data to a network server; connecting the pulse oximeter to a patient monitoring device; acquiring the connected pulse oximeter identification data and status data via the patient monitoring device; acquiring and storing pulse oximeter data using the connected pulse oximeter; transmitting the acquired pulse oximeter data, the acquired pulse oximeter identification data, and the acquired status data to the network server; matching the transmitted pulse oximeter identification data (Continued)

with the uploaded pulse oximeter identification data stored in the network server; and associating the transmitted pulse oximeter data to the patient information.

12 Claims, 7 Drawing Sheets

(56) References Cited

U.S. PATENT DOCUMENTS

| | | | |
|---|---|---|---|
| 2007/0043278 A1* | 2/2007 | Mannheimer | A61B 5/14552 |
| | | | 600/323 |
| 2011/0082711 A1 | 4/2011 | Poeze | |
| 2011/0307284 A1 | 12/2011 | Thompson | |
| 2013/0023719 A1 | 1/2013 | Bennett | |
| 2013/0087609 A1 | 4/2013 | Nochol | |
| 2013/0275155 A1 | 10/2013 | Miko | |
| 2013/0311104 A1* | 11/2013 | Inoue | G16H 10/60 |
| | | | 702/19 |
| 2014/0207489 A1 | 7/2014 | Wartena | |
| 2014/0236634 A1 | 8/2014 | Herbst | |
| 2016/0136356 A1* | 5/2016 | Ribble | A61B 5/6852 |
| | | | 604/111 |
| 2017/0014035 A1* | 1/2017 | Newberry | A61B 5/02 |

FOREIGN PATENT DOCUMENTS

| | | |
|---|---|---|
| WO | 0217778 | 3/2002 |
| WO | 2013176988 | 11/2013 |
| WO | 2014/119575 | 8/2014 |
| WO | 2014144208 | 9/2014 |
| WO | 2015091302 | 6/2015 |

* cited by examiner

TRACKING USAGE OF A PULSE OXIMETER VIA A NETWORK SYSTEM

CROSS REFERENCE TO RELATED APPLICATIONS

This application is the U.S. National Phase application under 35 U.S.C. § 371 of International Application No. PCT/EP2016/077232, filed Nov. 10, 2016, published as WO 2017/089139 on Jun. 1, 2017, which claims the benefit of European Patent Application Number 16160943.3 filed Mar. 17, 2016 and U.S. Provisional Patent Application No. 62/259,064 filed Nov. 24, 2015. These applications are hereby incorporated by reference herein.

BACKGROUND OF THE INVENTION

The tracking of medical devices' usage is vital in providing effective health care services. The task of tracking each medical device in a busy hospital environment can be taxing for a medical personnel. Automation of this task can now be accomplished by connecting medical devices into a network. Thus, medical personnel can readily access medical-related information and data acquired by medical devices locally or remotely.

Typically, in order to associate the acquired data to a patient, a medical personnel has to manually input patient information into the medical device. This can be a tedious process especially where a patient has to be moved to various hospital premises frequently and has to undergo different tests using different medical devices. This problem can be partly addressed through the use of disposable mobile medical devices that a patient can carry at all times. Medical devices have identification data assigned to them by manufacturers. Identification data can be a label affixed to the medical device such as a barcode, a QR code, or an RFID tag. By assigning the use of a disposable mobile medical device to only one patient, the automated tracking of medical device usage can be improved.

U.S. patent application number 2013/0087609 discloses methods for tracking medical devices, which comprise a 2D matrix code that can be scanned to obtain information about the device such as a name, a serial number, a make, a model, a date of manufacture, an owner, and an original location of installation. This information is transmitted to a computer system. The computer system then connects to the Internet that enables the monitoring and tracking of the medical device.

US 2004/102683 A1 discloses a patient monitoring system which provides a wireless communication link between a patient monitoring device, worn by a patient, and a local hub. The patient monitoring system is adapted to monitor various patient physiological characteristics, such as blood pressure, pulse rate, blood glucose, weight, pulse oximetry and others. The data from the patient monitoring device is wirelessly transmitted to a local hub, which, in turn, is configured to automatically transfer the data to a remote server, for example, over a public or private communications network. The server is configured as a web portal to selectively allow access to such patient physiological data by designated third parties, such as physicians, clinicians, relatives and the patient themselves. The system is also configured to provide reminders to patients to take readings.

SUMMARY OF THE CLAIMED INVENTION

According to aspects of the present invention there are presented a method and system for tracking usage of a pulse oximeter via a network system as defined in the claims. Further, a non-transitory computer-readable storage medium is presented.

The present invention relates to a method for medical device usage via a network system. In particular, the medical device can be a vital sign measurement device such as a pulse oximeter, blood pressure monitor, respiration monitor, temperature monitor, and the like. Patient information with corresponding vital sign data such as pulse oximeter identification data are uploaded to a network server. Once the pulse oximeter is connected to a patient monitoring device, the patient monitoring device acquires the pulse oximeter identification data and status data. Afterwards, pulse oximeter data are acquired from a patient and stored in the patient monitoring device. The acquired pulse oximeter data, acquired pulse oximeter identification data, and acquired status data are transmitted to the network server. The transmitted pulse oximeter identification data are matched with the uploaded pulse oximeter identification data stored in the network server. Once a match is found, the transmitted pulse oximeter data are associated with the corresponding patient information.

The present invention also relates to a system for tracking pulse oximetry usage via a network system comprising a pulse oximeter for acquiring pulse oximeter data, a patient monitoring device for acquiring pulse oximeter identification data and status data, and a network server for storing patient information with corresponding pulse oximeter identification data.

BRIEF DESCRIPTION OF THE DRAWINGS

The accompanying drawings, which are included to provide a further understanding of the invention, are incorporated herein to illustrate embodiments of the invention. Along with the description, they also serve to explain the principle of the invention. In the drawings.

DETAILED DESCRIPTION OF THE EMBODIMENTS

The following are definitions of terms as used in the various embodiments of the present invention.

The term "patient information" as used herein refers to data or information for identifying an individual. "Patient information" comprise at least one of patient's name, age, weight, previous medical history, admission number, medical personnel in charge, date of admission, medical condition or status, among others.

The term "identification data" as used herein refers to data and information for identifying a device. "Identification data" comprise at least one of a serial number, a product type, a product name, a product model number, a manufacturer name, and a date of manufacture, among others.

The term "status data" as used herein refers to data and information describing the state of a device. "Status data" describes if the device is connected, disconnected, in-use, or malfunctioning, among others.

The term "database" as used herein refers to a collection of data and information organized in such a way as to allow the data and information to be stored, retrieved, updated, and manipulated and to allow them to be presented into one or more formats such as in table form or to be grouped into text, numbers, images, and audio data. The term "database" as used herein may also refer to a portion of a larger database, which in this case forms a type of database within a database. "Database" as used herein also refers to conventional databases that may reside locally or that may be accessed from a remote location, e.g., remote network servers. The database typically resides in computer memory that includes various types of volatile and non-volatile computer memory. Memory wherein the database resides may include high-speed random access memory or non-volatile memory such as magnetic disk storage devices, optical storage devices, and flash memory. Memory where the database resides may also comprise one or more software for processing and organizing data received by and stored into the database.

The present invention relates to a method for tracking usage of a pulse oximeter via a network system comprising: uploading a patient information with corresponding pulse oximeter identification data to a network server; connecting the pulse oximeter to a patient monitoring device; acquiring the connected pulse oximeter identification data and status data via the patient monitoring device; acquiring and storing pulse oximeter data using the connected pulse oximeter; transmitting the acquired pulse oximeter data, the acquired pulse oximeter identification data, and the acquired status data to the network server; matching the transmitted pulse oximeter identification data with the uploaded pulse oximeter identification data stored in the network server; and associating the transmitted pulse oximeter data to the patient information.

The present invention also relates to a system for tracking usage of a pulse oximeter via a network system comprising: a pulse oximeter for acquiring pulse oximeter data; a patient monitoring device for acquiring pulse oximeter identification data and status data; and a network server for storing patient information with corresponding pulse oximeter identification data.

Figure 1:
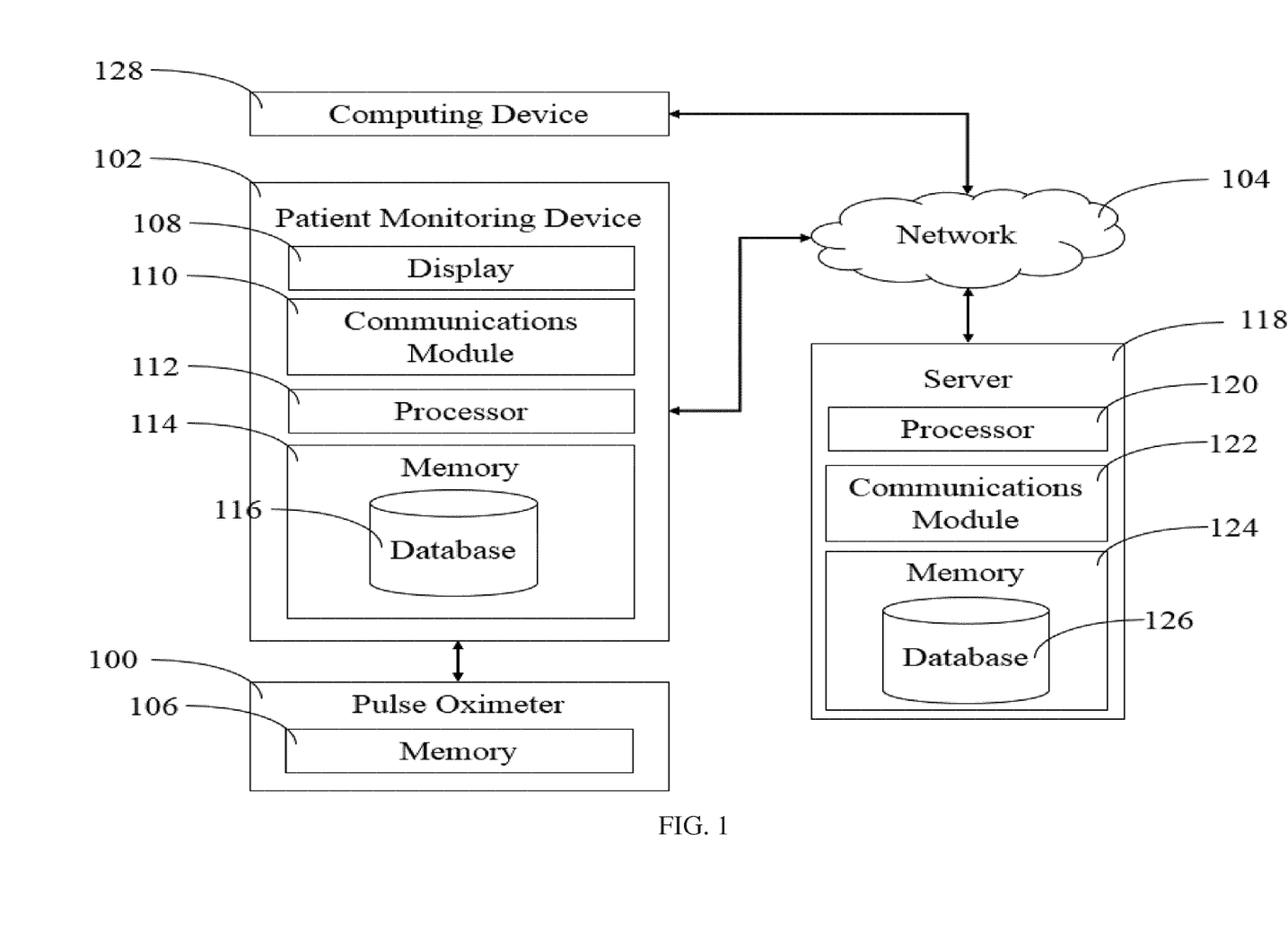
FIG. 1 illustrates a block diagram of a system for tracking pulse oximetry usage via a network system according to a preferred embodiment of the present invention.

FIG. 1 illustrates a preferred embodiment of a system for tracking usage of a pulse oximeter via a network system. The system comprises a pulse oximeter 100 connected to a patient monitoring device 102, which, in turn, is connected to a network 104. The pulse oximeter 100 comprise a memory 106 for storing pulse oximeter identification data. The patient monitoring device 102 comprises a display 108, a communications module 110, a processor 112, and a memory 114. The memory 114 further comprises a database 116. Also connected to the network 104 is a server 118. The server 118 comprises a processor 120, a communications module 122, and a memory 124. The memory 124 comprises a database 126.

The pulse oximeter 100 preferably measures at least one of blood oxygen saturation, pulse rate, perfusion index, and respiration rate. Blood oxygen saturation is a measure of the amount of oxygen carried by hemoglobin in the blood stream. It is usually expressed as a percentage rather than an absolute reading. For example, blood oxygen saturation levels measured immediately after birth can provide a good indicator of a baby's general state of health. Levels below 75% could indicate that the newborn infant may be suffering from some abnormality. To determine a patient's condition, the blood oxygen saturation should be expressed as a percentage of the total hemoglobin that is saturated with oxygen. Under many circumstances, that is the reading that pulse oximeters provides. Acceptable normal ranges for healthy patients range from 95 to 99 percent.

The pulse rate is the number of times the heart beats per minute. The pulse rate is characterized by the peaks in the pleth waveform. Acceptable normal pulse rates for healthy patients range from 60 to 100 beats per minute (bpm). For example, a pulse rate of 40 bpm could indicate a simple low blood pressure or bradycardia. On the other hand, a pulse rate of 100 bpm or more could indicate a fever or low blood sugar. When the pulse rate is irregular, it could indicate arrhythmia which could cause the heart not being able to pump enough blood to the body.

The perfusion index is a ratio of the pulsatile blood flow to the non-pulsatile static blood flow in a patient's peripheral tissue. Perfusion index is an indication of the pulse strength wherein values range from 0.02% for weak pulse strength to 20% for strong pulse strength.

The respiration rate is the number of breaths per minute. The respiration rate is based on changes in the cardiovascular, respiratory and autonomic nervous systems that affects the pleth waveform. These changes can be used to calculate the respiration rate. Acceptable normal ranges for healthy patients range from 12 to 20 breaths/minute. Abnormal ranges of respiration rate may indicate asthma, pneumonia, congenital heart disease or drug overdose.

Figure 2:
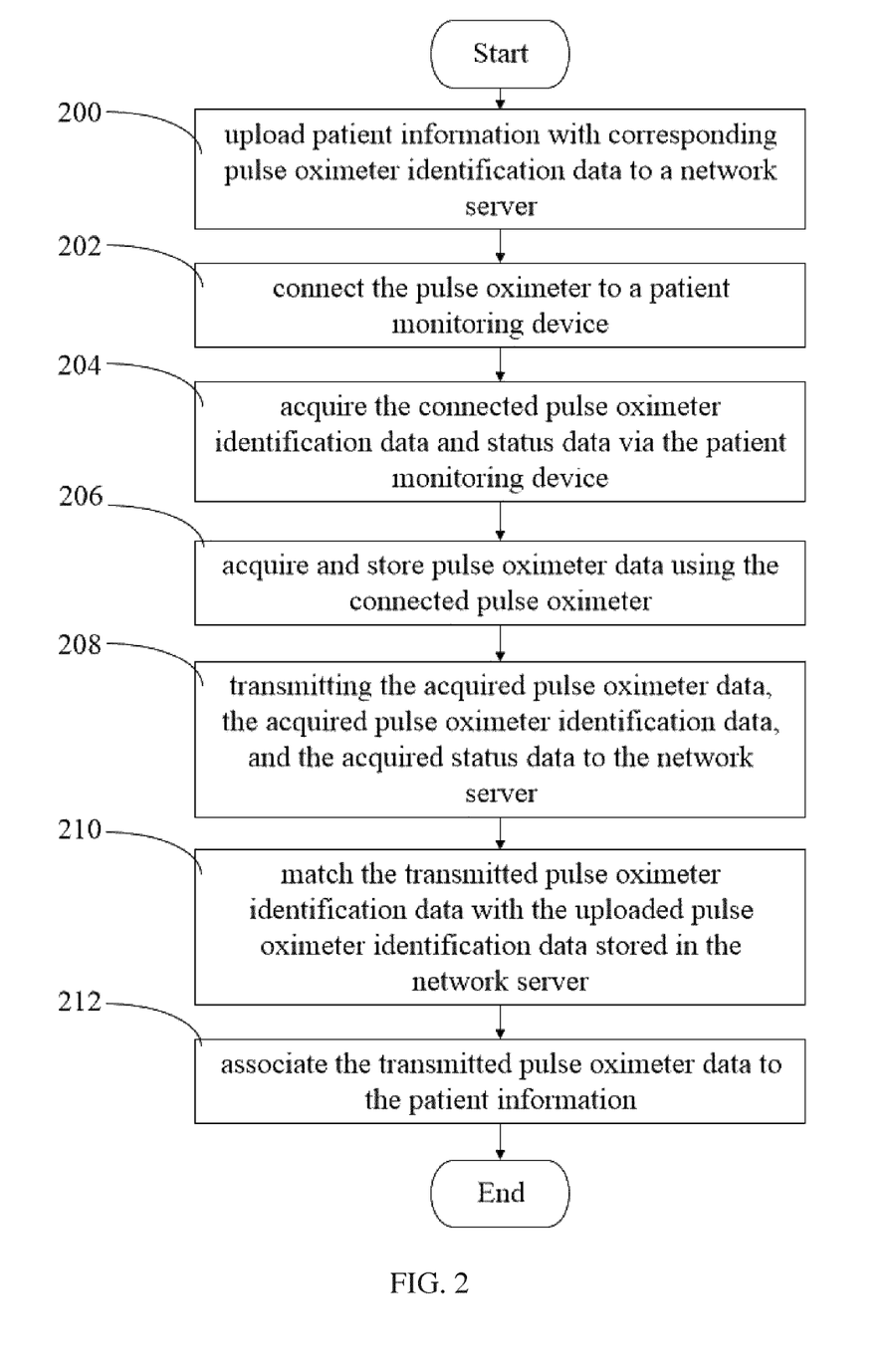
FIG. 2 is a flowchart according to a preferred embodiment of the present invention.

FIG. 2 illustrates a preferred method of the present invention. Patient information with corresponding pulse oximeter identification data are uploaded to a network server 118 (step 200). When a patient is admitted to a healthcare facility, a portable pulse oximeter 100 is assigned to the patient. Each portable pulse oximeter in the healthcare facility has pulse oximeter identification data, for example, a serial identification number. A medical personnel, using a computing device 128, manually inputs the assigned pulse oximeter's serial identification number and patient information such as the patient's name. The given information are then uploaded and stored in the network server's database 126. In an alternative embodiment, the pulse oximeter identification data are acquired by scanning a machine-readable indicia, such as a barcode, a QR code, or an RFID tag, among others.

In another embodiment, the pulse oximeter 100 is connected to the computing device 128 via wireless or wired connection. The computing device 128 then accesses the pulse oximeter's memory 106 and acquires the pulse oximeter's serial identification number.

In yet another embodiment, a list of serial identification numbers of various pulse oximeters are stored in network server's database 126. The medical personnel accesses the database 126 and acquires an assigned pulse oximeter's serial identification number via the computing device 128. The medical personnel then inputs the name of the patient assigned to use that particular pulse oximeter. Afterwards, the database 126 is updated with the given information.

From FIG. 2, when the pulse oximeter 100 is connected to a patient monitoring device 102 (step 202), the patient monitoring device 102 acquires the connected pulse oximeter identification data by accessing the pulse oximeter's memory 106 (step 204). The patient monitoring device 102 also acquires the pulse oximeter status data (step 204). Afterwards, the patient's pulse oximeter parameters are measured and then stored in the patient monitoring device's database 116 (step 206). Connection and data transmission from the pulse oximeter 100 to the patient monitoring device 102 may be accomplished using wired or wireless technology. The acquired pulse oximeter data, acquired pulse oximeter identification data, and acquired status data are then transmitted to the network server's database 126 (step 208). Subsequently, the transmitted pulse oximeter identification data are matched with the uploaded pulse oximeter identification data stored in the network server's database 126 (step 210). Once a match is found, the transmitted pulse oximeter data are associated to the patient information (step 212).

Figure 3:
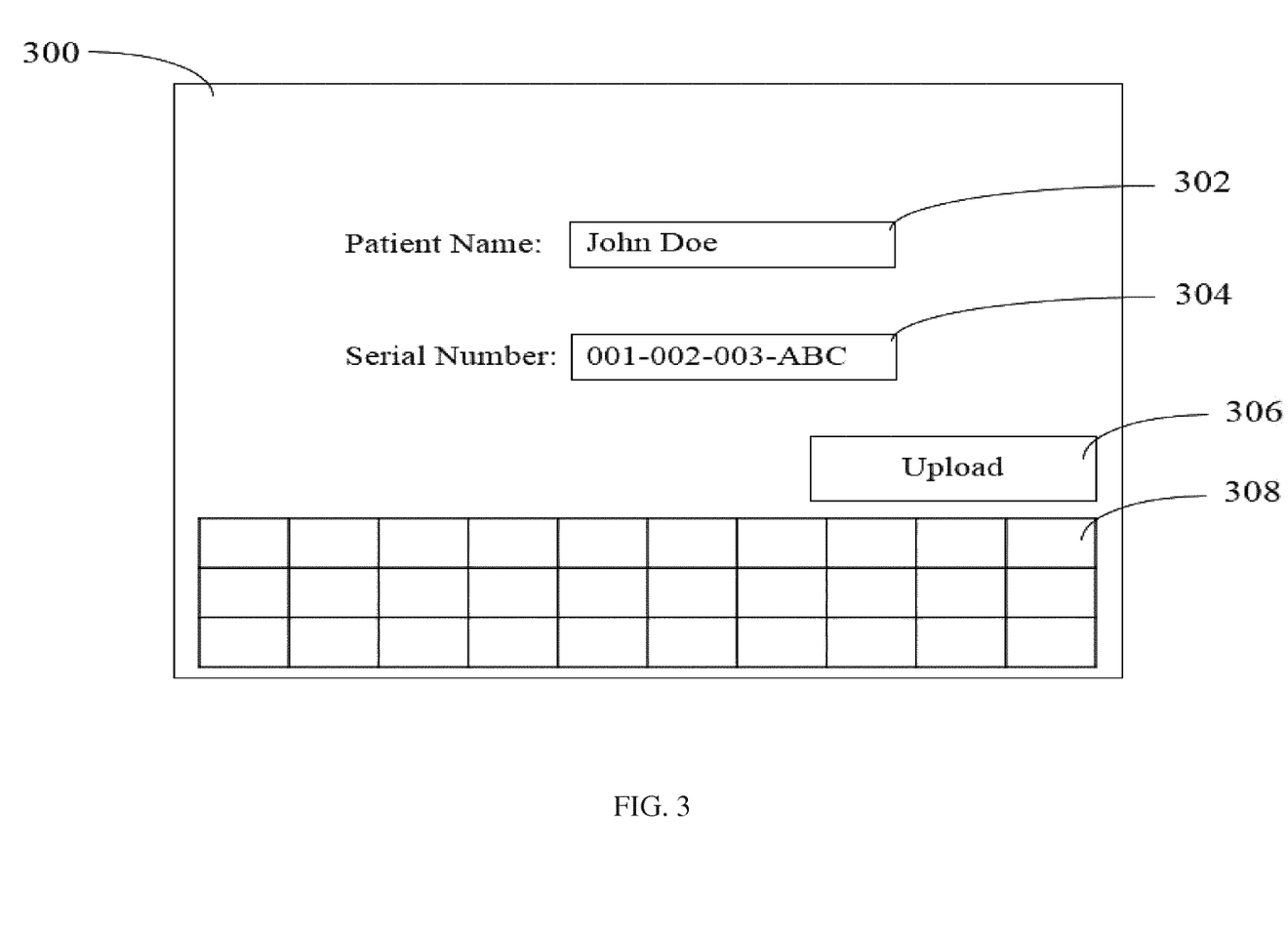
FIG. 3 illustrates an embodiment of a graphical user interface window for assigning patient information to pulse oximeter identification data according to the present invention.

FIG. 3 illustrates an embodiment of a graphical user interface window for assigning patient information to a pulse oximeter identification data. The patient set-up GUI window 300 comprises input fields 302 and 304 wherein a medical personnel can enter patient information and pulse oximeter identification data, respectively. In the case shown in FIG. 3, the medical personnel enters the patient's name and the pulse oximeter's serial number. The window 300 further comprises an upload button 306 for saving the entered information to the network server's database 126. The window 300 optionally comprises a keyboard 308 that enables the medical personnel to input the required information via touchscreen.

Figure 4:
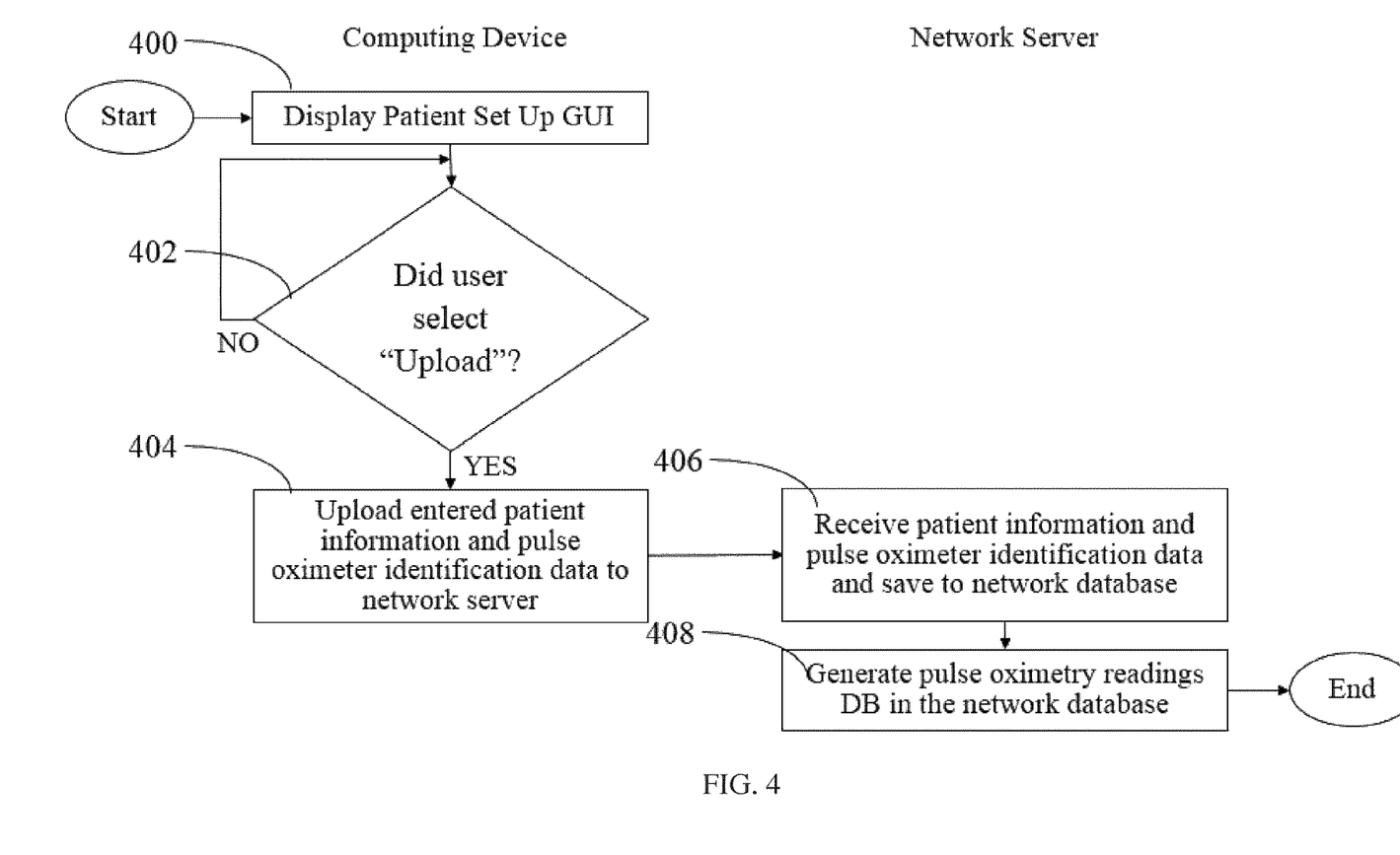
FIG. 4 illustrates a method for uploading patient information with corresponding pulse oximeter identification data to a network server according to the present invention.

FIG. 4 illustrates a method for uploading patient information with corresponding pulse oximeter identification data to a network server according to the present invention. The process starts by displaying on the computing device 128 the patient set-up GUI window 300, which allows the medical personnel to input patient information and pulse oximeter identification data (step 400). The computing device 128 is repeatedly polled until the medical personnel selects the "Upload" option (step 402). When "Upload" has been selected, the entered information in the patient set-up GUI window 300 are uploaded to the network database 126 (step 406-408). Thereafter, a pulse oximeter readings database for storing acquired pulse oximeter data is generated within the network database 126 (step 408).

Figure 5:
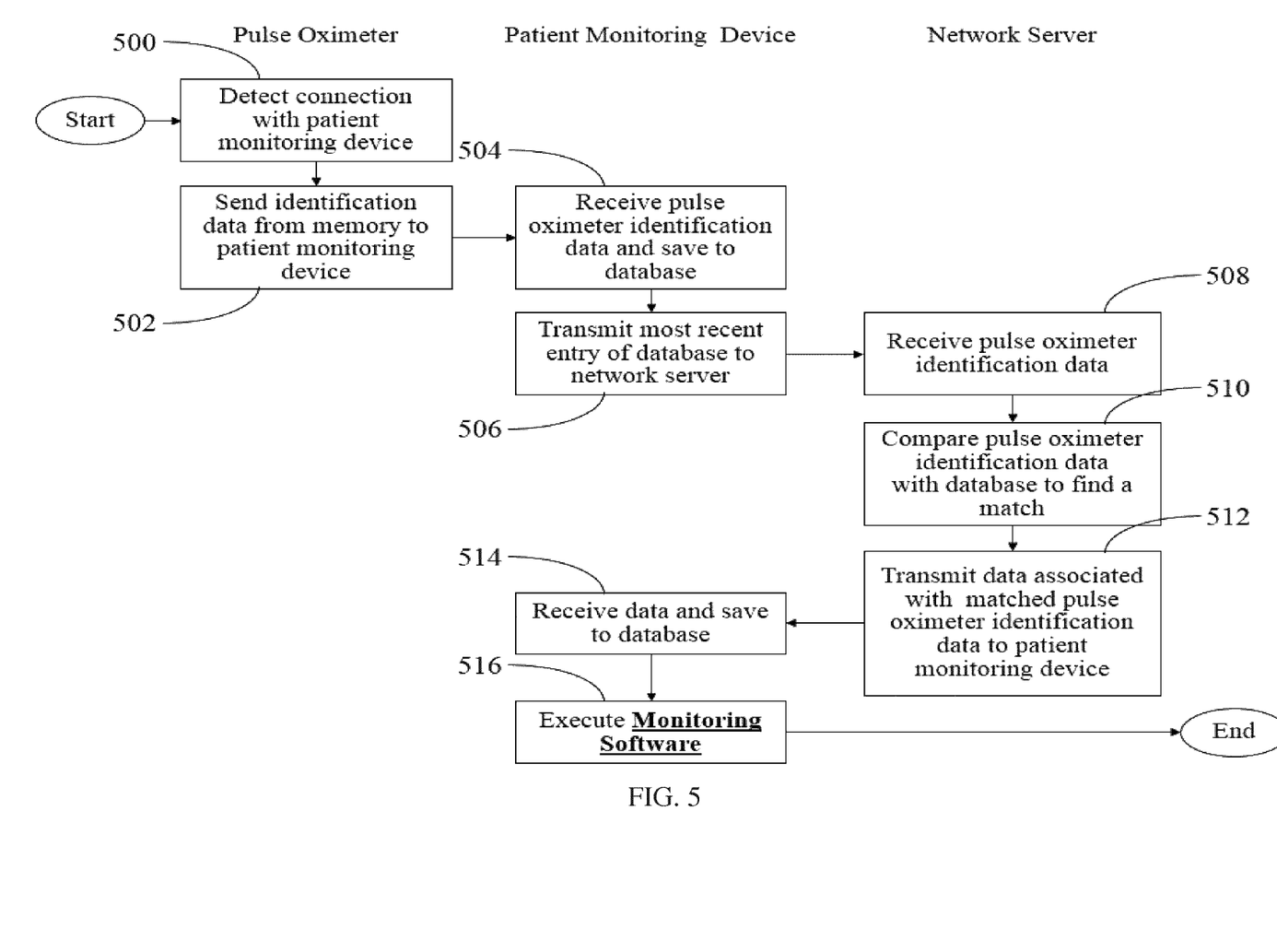
FIG. 5 illustrates a method for tracking usage of a pulse oximeter via a network system according to the present invention.

FIG. 5 illustrates a method for tracking pulse oximeter usage via a network system according to the present invention. In the first step, a medical personnel connects the pulse oximeter 100 to the patient monitoring device 102. Once the pulse oximeter 100 detects a connection with the patient monitoring device 102 (step 500), the pulse oximeter identification data stored in the pulse oximeter's memory 106 is transmitted and saved to the patient monitoring device's database 116 (steps 502-504). In turn, the patient monitoring device 102 transmits the pulse oximeter identification data to the network server 118 (steps 506-508) where the pulse oximeter identification data is compared with data within the network server's database 126 (step 510). If a match is found, data associated with the matched pulse oximeter identification data, such as patient information, are transmitted and saved to the patient monitoring device's database 116 (steps 512-514). Afterwards, a monitoring software is executed by the patient monitoring device 102 (step 516).

Figure 6:
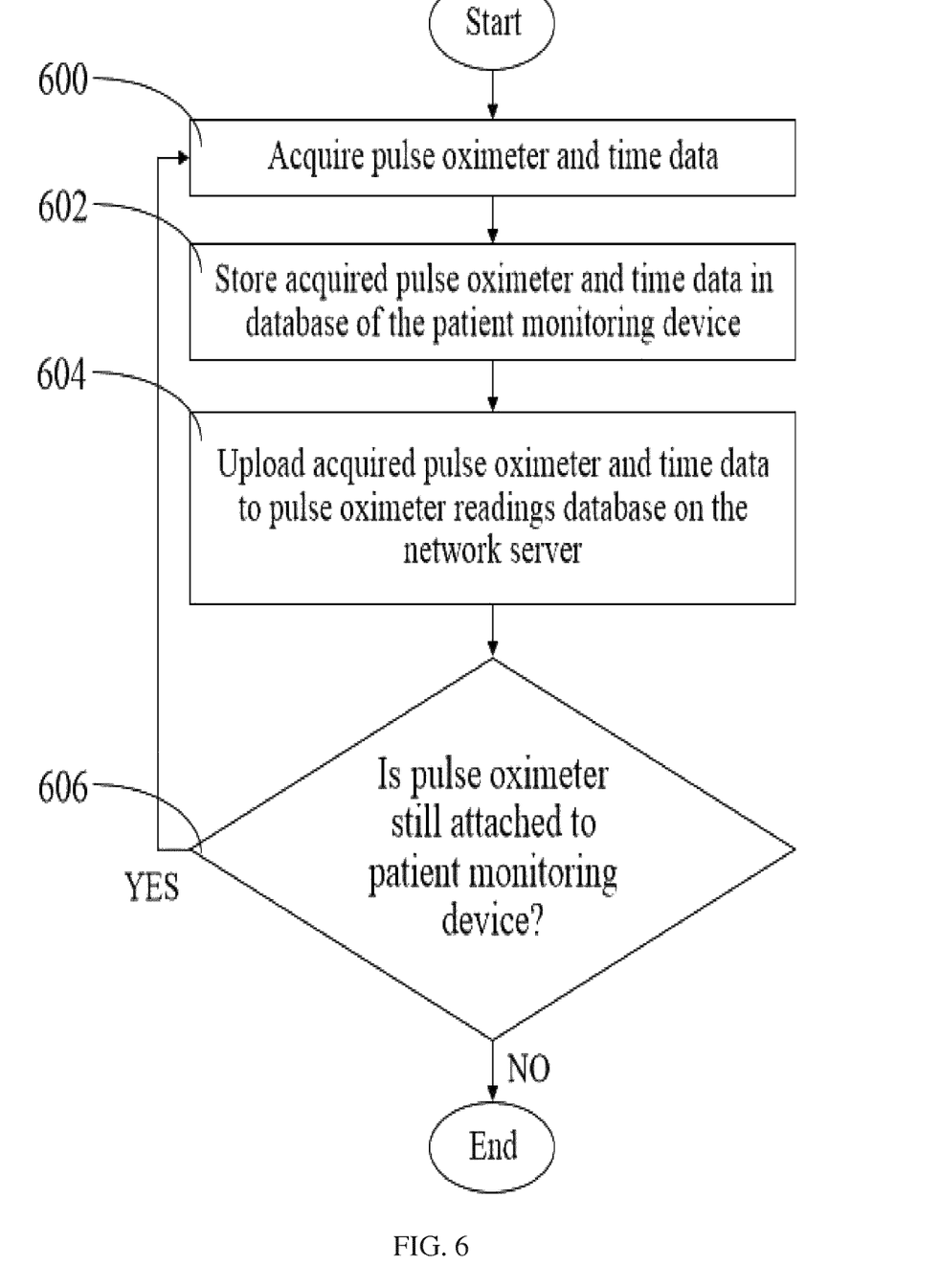
FIG. 6 illustrates a method involving a monitoring software for according to the present invention.

FIG. 6 illustrates a method involving a monitoring software according to the present invention. First, pulse oximeter and time data are acquired, transmitted, and stored in the patient monitoring device's database 116 (steps 600-602). The pulse oximeter and time data are then uploaded to the pulse oximeter readings database stored within the network server's database 126 (step 604). Afterwards, the patient monitoring device 102 determines if the pulse oximeter 100 is still connected (step 606). If so, the software loops back to acquire pulse oximeter and time data (step 600). Otherwise, the software is terminated.

In one embodiment, status data regarding the state of the pulse oximeter 100 are generated by the patient monitoring device 102. For example, patient monitoring device 102 records the time when the pulse oximeter 100 is connected and disconnected. Status data are then transmitted to the network server's database 126.

From the status data, information about the pulse oximeter 100 can be extracted such as the number of times the pulse oximeter 100 has been used and the amount of time the pulse oximeter 100 has been in-use. This data can be used in the maintenance of the pulse oximeter 100. The extracted information is then saved in the network server's memory 124 and can be accessed using a computing device 128 via network 104.

In another embodiment, data from the pulse oximeter readings database stored in the network server's database 126 are transmitted to the patient monitoring device's database 116. This allows the medical personnel to view past pulse oximeter data acquired from another patient monitoring device.

Figure 7A:
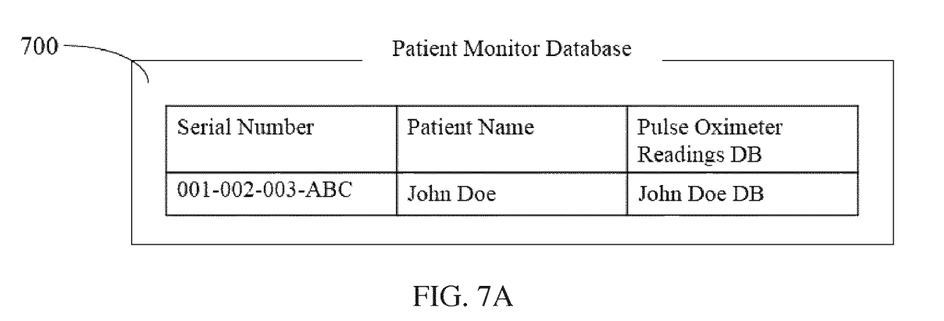
FIG. 7A illustrates an embodiment of the data stored in the patient monitoring device's database.
Figure 7B:
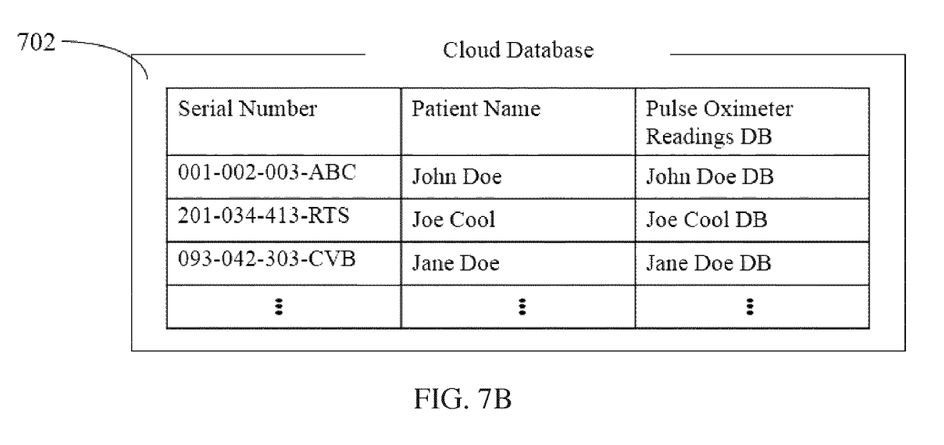
FIG. 7B illustrates an embodiment of the data stored in the network server's database.

FIG. 7A and FIG. 7B illustrate an exemplary embodiment of the data stored in the patient monitoring device's database 700 and network server's database 702, respectively. For both databases, pulse oximeter identification data, patient information, and pulse oximetry data are organized in table form. Patient monitoring device's database 700, as shown in FIG. 7A, comprises the connected pulse oximeter's serial number, the patient name, and a pulse oximetry readings database. On the other hand, network server's database 702, as shown in FIG. 7B, comprises a list of pulse oximeter serial numbers, a list of patient names, and a list of pulse oximetry readings databases.

In an exemplary embodiment of the invention, using the information from FIGS. 7A and 7B, patient "John Doe" is admitted to a hospital for surgery and was given a disposable pulse oximeter with serial number "001-002-003-ABC." A nurse, using a computer, inputs the patient's name and the serial number of the pulse oximeter in the GUI. The nurse then uploads the information to the cloud database 702. Within the cloud database, a new database "John Doe DB" is generated. "John Doe DB" at this point does not yet contain any data.

As the patient settles into one of the hospital's patient room, the nurse connects the pulse oximeter to a patient monitor installed in the room. Once connected, the patient monitor acquires the pulse oximeter's serial number "001-002-003-ABC." The patient monitor then accesses the cloud network and determines that for the acquired serial number for that particular pulse oximeter, the patient being monitored is "John Doe." The pulse oximeter's serial number "001-002-003-ABC" and the patient's name "John Doe" are stored temporarily in the patient monitor database 700. Afterwards, the patient monitor retrieves the data from the "John Doe DB" database of the cloud database 702 and temporarily stores it in the patient monitor database 700. The patient's pulse oximeter parameter are measured via the pulse oximeter. The pulse oximeter data are then stored to "John Doe DB" database, which is stored in the patient monitor database 700.

As the time for the surgery approaches, the patient is transferred to the surgery room. The pulse oximeter is disconnected from the patient monitor installed in the patient's room. Once disconnected, the "John Doe DB" data stored in the patient monitor database 700 is transmitted to the cloud network and updates the "John Doe DB" database that resides in the cloud database 702. Data corresponding to "John Doe" in the patient monitor database 700 are then erased. At the surgery room, the nurse connects the pulse oximeter to a patient monitor installed in the surgery room. The process as described above is repeated until the pulse oximeter is again disconnected. After the data has been saved in the cloud, a doctor reviewing the case can easily access the data using any computing device connected to the cloud.

The present invention is not intended to be restricted to the several exemplary embodiments of the invention described above. Other variations that may be envisioned by those skilled in the art are intended to fall within the disclosure. For example, while the foregoing description is particular to pulse oximeters, it is to be understood that other vital sign sensors and monitors could also be implemented.

The invention claimed is:

1. A method for tracking usage of a pulse oximeter via a network system, the method comprising:
   storing patient information and pulse oximeter identification data identifying the pulse oximeter associated with the patient, wherein the patient information and pulse oximeter identification data are stored at a network server;
   connecting the pulse oximeter to a patient monitoring device, wherein the patient monitoring device is provided with the pulse oximeter identification data and status data;
   monitoring pulse oximeter data using the connected pulse oximeter for measuring the pulse oximeter data;
   transmitting the pulse oximeter data, the pulse oximeter identification data, and the status data from the patient monitoring device to the network server;
   matching the transmitted pulse oximeter identification data with the pulse oximeter identification data stored in the network server;
   associating the transmitted pulse oximeter data to the stored patient information;
   transmitting past pulse oximeter data matched with the transmitted pulse oximeter identification data from the network server to the patient monitoring device, wherein the past pulse oximeter data is from a second patient monitoring device connected to a second pulse oximeter, and wherein the pulse oximeter is a first pulse oximeter different from the second pulse oximeter and the patient monitoring device is a first patient monitoring device different from the second patient monitoring device;
   displaying the past pulse oximeter data from the second patient monitoring device on the first patient monitoring device; and
   storing received past pulse oximeter data to a patient monitoring device database.

2. The method of claim 1, further comprising uploading the patient information and pulse oximeter identification data to the network server.

3. The method of claim 2, wherein pulse oximeter identification data is uploaded to the network server by scanning a coded image.

4. The method of claim 3, wherein the coded image is one of a barcode, a QR code, or an RFID tag.

5. The method of claim 1, wherein another patient monitoring device accesses the patient monitoring device database to obtain the past pulse oximeter data.

6. The method of claim 1, wherein the status data includes information regarding the state of the pulse oximeter, the state of the device being at least one of 'connected', 'disconnected', 'in-use' or 'malfunctioning'.

7. A system for tracking usage of a pulse oximeter via a network system, the system comprising:
   a pulse oximeter that measures pulse oximeter data;
   a patient monitoring device that obtains pulse oximeter identification data, status data and pulse oximeter data from the pulse oximeter connected to the patient monitoring device; and
   a network server that stores patient information and pulse oximeter identification data identifying the pulse oximeter associated with the patient,
   wherein the patient monitoring device is configured to transmit the pulse oximeter data, the pulse oximeter identification data, and the status data to the network server,
   wherein the network server is configured to match the transmitted pulse oximeter identification data with the pulse oximeter identification data stored in the network server, to associate the transmitted pulse oximeter data to the stored patient information, and to transmitting past pulse oximeter data matched with the transmitted pulse oximeter identification data to the patient monitoring device, wherein the past pulse oximeter data is from a second patient monitoring device connected to a second pulse oximeter, and wherein the pulse oximeter is a first pulse oximeter different from the second pulse oximeter and the patient monitoring device is a first patient monitoring device different from the second patient monitoring device, and
   wherein the patient monitoring device is configured to display the past pulse oximeter data from the second patient monitoring device on the first patient monitoring device and to store received past pulse oximeter data to a patient monitoring device database.

8. The system of claim 7, further comprising uploading the patient information and pulse oximeter identification data to the network server.

9. The system of claim 8, wherein pulse oximeter identification data is uploaded to the network server by scanning a coded image.

10. The system of claim 9, wherein the coded image is one of a barcode, a QR code, or an RFID tag.

11. The system of claim 7, wherein the status data includes information regarding the state of the pulse oximeter, the state of the device being at least one of 'connected', 'disconnected', 'in-use' or 'malfunctioning'.

12. A non-transitory computer-readable storage medium, having embodied thereon a program executable by a processor to perform a method for tracking usage of a pulse oximeter via a network system, the method comprising:
   storing patient information and pulse oximeter identification data identifying the pulse oximeter associated with the patient, wherein the patient information and pulse oximeter identification data are stored at a network server;

connecting the pulse oximeter to a patient monitoring device, wherein the patient monitoring device is provided with the pulse oximeter identification data and status data;

monitoring pulse oximeter data using the connected pulse oximeter for measuring the pulse oximeter data;

transmitting the pulse oximeter data, the pulse oximeter identification data, and the status data from the patient monitoring device to the network server;

matching the transmitted pulse oximeter identification data with the pulse oximeter identification data stored in the network server;

associating the transmitted pulse oximeter data to the stored patient information;

transmitting past pulse oximeter data matched with the transmitted pulse oximeter identification data from the network server to the patient monitoring device, wherein the past pulse oximeter data is from a second patient monitoring device connected to a second pulse oximeter, and wherein the pulse oximeter is a first pulse oximeter different from the second pulse oximeter and the patient monitoring device is a first patient monitoring device different from the second patient monitoring device;

displaying the past pulse oximeter data from the second patient monitoring device on the first patient monitoring device; and storing received past pulse oximeter data to a patient monitoring device database.

* * * * *